United States Patent
Vraspir et al.

(10) Patent No.: US 10,611,793 B1
(45) Date of Patent: Apr. 7, 2020

(54) SOLID STATE FORMS OF OBETICHOLIC ACID SALTS

(71) Applicant: Teva Czech Industries s.r.o., Opava-Komarov (CZ)

(72) Inventors: Pavel Vraspir, Rymarov (CZ); Jiri Faustmann, Opava-Kylesovice (CZ)

(73) Assignee: TEVA CZECH INDUSTRIES S.R.O., Opava-Komarov (CZ)

( * ) Notice: Subject to any disclaimer, the term of this patent is extended or adjusted under 35 U.S.C. 154(b) by 0 days.

(21) Appl. No.: 16/201,053

(22) Filed: Nov. 27, 2018

Related U.S. Application Data (60) Provisional application No. 62/646,998, filed on Mar. 23, 2018, provisional application No. 62/590,779, filed on Nov. 27, 2017.

(51) Int. Cl.
*C07J 9/00* (2006.01)

(52) U.S. Cl.
CPC ........... *C07J 9/005* (2013.01); *C07B 2200/13* (2013.01)

(58) Field of Classification Search
CPC ....................................................... C07J 9/00
See application file for complete search history.

(56) References Cited

U.S. PATENT DOCUMENTS

| | | | |
|---|---|---|---|
| 7,138,390 B2 | 11/2006 | Pellicciari | |
| 9,238,673 B2 | 1/2016 | Steiner et al. | |
| 9,732,117 B2 * | 8/2017 | Pellicciari | C07J 9/00 |
| 2016/0108082 A1 * | 4/2016 | Steiner | A61K 31/00 552/553 |
| 2018/0099991 A1 | 4/2018 | Sanphui et al. | |

FOREIGN PATENT DOCUMENTS

| | | |
|---|---|---|
| CZ | 2016222 | 10/2017 |
| WO | 2016046680 A2 | 3/2016 |
| WO | 2017137931 A1 | 8/2017 |
| WO | 2018165269 A2 | 9/2018 |

OTHER PUBLICATIONS

G.P. Stahly, 7 Crystal Growth & Design, 1007-1026 (2007).*
Lee et al., 2 Annual Review of Chemical and Biomolecular Engineering, 259-280 (2011).*
H.G. Brittain, In Polymorphism in Pharmaceutical Solids (H.G. Brittain ed., 2nd ed., (2009).*
S.L. Morissette et al., 56 Advanced Drug Delivery Reviews, 275-300, 276, (2004).*
Otyepková, Eva and Gabriel, Roman; "Krystalické Soli Kyseliny Obeticholové"; Chem. Listy, vol. 113, Jul. 15, 2019, p. 434-437.

* cited by examiner

*Primary Examiner* — Alexander R Pagano
*Assistant Examiner* — Ebenezer O Sackey
(74) *Attorney, Agent, or Firm* — Cantor Colburn LLP (57) ABSTRACT

Disclosed are salts of obeticholic acid, solid state forms thereof, processes for preparation thereof, and use thereof in the preparation of pharmaceutical compositions or the preparation of a different solid state form of obeticholic acid or salt thereof, and use in methods of treating liver diseases, e.g. primary biliary cirrhosis (PBC) and nonalcoholic steatohepatitis (NASH).

14 Claims, 7 Drawing Sheets

Figure 1 shows a PXRD pattern of crystalline form A of 3-aminopentane salt of obeticholic acid.

Figure 2 shows a PXRD pattern of crystalline form A of (S)-aminoquinuclidine salt of obeticholic acid.

Figure 3 shows a PXRD pattern of crystalline form A of N-methyl propyl amine salt of obeticholic acid.

Figure 5 shows a PXRD pattern of crystalline form B of tetrabutylammonium salt of obeticholic acid Figure 7 shows a FTIR spectrum of crystalline form A of 3-aminopentane salt of obeticholic acid in range 1800 – 550 cm$^{-1}$

SOLID STATE FORMS OF OBETICHOLIC ACID SALTS

CROSS-REFERENCE TO RELATED APPLICATIONS

This application claims the benefit of U.S. Provisional Application No. 62/590,779, filed Nov. 27, 2017 and U.S. Provisional Application No. 62/646,998, filed Mar. 23, 2018, both of which are incorporated by reference herein in their entirety.

FIELD OF THE INVENTION

The present disclosure relates to salts of obeticholic acid, solid state forms thereof, processes for preparation thereof and use thereof in the preparation of pharmaceutical compositions.

BACKGROUND OF THE INVENTION

Obeticholic acid has the chemical name (3α,5β,6α,7α)-6-ethyl-3,7-dihydroxycholan-24-oic acid. Obeticholic acid has the following chemical structure:

Obeticholic acid (abbreviated to OCA) is a semi-synthetic bile acid analogue which has the chemical name 6α-ethyl-chenodeoxycholic acid. Obeticholic acid is a Farnesoid X receptor agonist indicated for primary biliary cholangitis/cirrhosis (PBC) and being developed by Intercept Pharmaceuticals Inc. for the treatment of other liver conditions such as Non-alcoholic steatohepatitis (NASH).

Obeticholic acid is known from U.S. Pat. No. 7,138,390.

Obeticholic acid salts are known from U.S. Pat. No. 9,732,117, CZ 2016-222, WO 2016/046680, WO2017137931, and US20180099991.

Crystalline forms of obeticholic acid, a pharmaceutical composition comprising obeticholic acid Form 1 (non-crystalline form of obeticholic acid) and a pharmaceutically acceptable carrier, wherein the obeticholic acid Form 1 comprises less than 1% of chenodeoxycholic acid are described in U.S. Pat. No. 9,238,673.

(S)-α-methylbenzylamine and diethylamine salt of obeticholic acid and process for preparation of amorphous form by conversion of the salt to amorphous form of obeticholic acid are known from WO2017/137931. Obeticholic acid-Ursodeoxycholic acid cocrystal and obeticholic acid monoammonium salt are known from WO2018165269.

Polymorphism, the occurrence of different crystal forms, is a property of some molecules and molecular complexes. A single compound, like obeticholic acid or salt thereof, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, Raman absorption fingerprint, and solid state ($^{13}$C-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life.

In case of obeticholic acid, there are several known impurities. Therefore, there is a need for crystalline salt of obeticholic acid, useful in purification of obeticholic acid and suitable for industrial process.

SUMMARY OF THE INVENTION

The present disclosure relates to salts of obeticholic acid and solid state forms thereof, in particular to solid state forms of obeticholic acid salts, to processes for preparation thereof, and to pharmaceutical compositions comprising these solid state forms.

The present disclosure encompasses process for preparation of amorphous form of obeticholic acid comprising converting the salts of obeticholic acid and solid state forms thereof to amorphous form of obeticholic acid.

The present disclosure also provides uses of the salts of obeticholic acid and solid state forms thereof for preparing other solid state forms of obeticholic acid, other salts of obeticholic acid and solid state forms thereof.

In another embodiment, the present disclosure encompasses the above described salts of obeticholic acid and solid state forms thereof for use in the preparation of pharmaceutical compositions and/or formulations, preferably for the treatment of liver indications, e.g. primary biliary cirrhosis (PBC) and nonalcoholic steatohepatitis (NASH).

In another embodiment the present disclosure encompasses the use of the above described salts of obeticholic acid and solid state forms thereof for the preparation of pharmaceutical compositions and/or formulations.

The present disclosure further provides pharmaceutical compositions comprising obeticholic acid, including amorphous form prepared according to the present disclosure.

In yet another embodiment, the present disclosure encompasses pharmaceutical formulations comprising obeticholic acid, wherein the pharmaceutical composition or formulation comprises obeticholic acid in any solid state form, including amorphous form, prepared according to the present disclosure and further comprises at least one pharmaceutically acceptable excipient. The pharmaceutical composition or formulation comprises oral dosage forms, e.g. tablet or capsule.

The present disclosure encompasses processes to prepare said pharmaceutical formulations of obeticholic acid comprising combining obeticholic acid, including amorphous form, prepared according to the present disclosure with at least one pharmaceutically acceptable excipient. The salts of obeticholic acid and solid state forms as defined herein, as well as the pharmaceutical compositions or formulations of obeticholic acid prepared according to the present invention, can be used as medicaments, particularly for the treatment of liver diseases, e.g. primary biliary cirrhosis (PBC) and nonalcoholic steatohepatitis (NASH).

The present disclosure also provides methods of treating liver diseases, e.g. primary biliary cirrhosis (PBC) and nonalcoholic steatohepatitis (NASH); comprising administering a therapeutically effective amount of obeticholic acid prepared according to the present disclosure, or at least one of the above pharmaceutical compositions or formulations, to a subject suffering from liver disease, or otherwise in need of the treatment.

The present disclosure also provides uses of obeticholic acid salts and solid state forms thereof of the present disclosure, or at least one of the above pharmaceutical compositions or formulations for the manufacture of a medicament for treating liver diseases, e.g. primary biliary cirrhosis (PBC) and nonalcoholic steatohepatitis (NASH).

DETAILED DESCRIPTION OF THE INVENTION

The present disclosure relates to obeticholic acid salts and solid state forms thereof, in particular to solid state forms of obeticholic acid salts, processes for preparation thereof and use thereof in the preparation of pharmaceutical composition. The disclosure also relates to the conversion of the obeticholic acid salts and its solid state forms to other solid state forms of obeticholic acid e.g. amorphous form or to other salts of obeticholic acid and solid state forms thereof.

The salts of obeticholic acid and solid state forms thereof according to the present disclosure may have advantageous properties selected from at least one of: chemical or polymorphic purity, flowability, solubility, dissolution rate, bioavailability, morphology or crystal habit, stability such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Obeticholic acid or salts thereof referred to herein as being characterized by graphical data "as depicted in" a Figure will thus be understood to include any crystal forms of the Obeticholic acid or salts thereof, characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by PXRD. Thus, solid state of obeticholic acid or salts thereof described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state form of obeticholic acid or salts thereof. Accordingly, in some embodiments of the disclosure, the described solid state forms of obeticholic acid or salts thereof may contain from about 1% to about 20% (w/w), from about 5% to about 20% (w/w), or from about 5% to about 10% (w/w) of one or more other solid state forms of the same obeticholic acid.

The modifier "about" should be considered as disclosing the range defined by the absolute values of the two endpoints. For example, the expression "from about 2 to about 4" also discloses the range "from 2 to 4." When used to modify a single number, the term "about" may refer to plus or minus 10% of the indicated number and includes the indicated number. For example, "about 10%" may indicate a range of 9% to 11%, and "about 1" means from 0.9-1.1.

As used herein, unless stated otherwise, PXRD peaks reported herein are preferably measured using CuK$_\alpha$ radiation, $\lambda$=1.5418 Å.

As used herein, the term "isolated" in reference to solid state forms of obeticholic acid or salts thereof of the present disclosure corresponds to solid state forms of obeticholic acid or salts thereof that are physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, and unless stated otherwise, the term "anhydrous" in relation to crystalline obeticholic acid or salts thereof relates to a crystalline obeticholic acid or salts thereof which does not include any crystalline water (or other solvents) in a defined, stoichiometric amount within the crystal. Moreover, an "anhydrous" form does not contain more than 1% (w/w) of either water or organic solvents as measured for example by TGA.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, etc.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, etc.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

The present disclosure comprises 3-aminopentane salt of obeticholic acid. Specifically, the present disclosure comprises crystalline 3-aminopentane salt of obeticholic acid.

The present disclosure further comprises a crystalline form of 3-aminopentane salt of obeticholic acid designated as Form A. The crystalline Form A of 3-aminopentane salt of obeticholic acid can be characterized by data selected from one or more of the following: a PXRD pattern having peaks at 5.3, 8.5, 10.8, 11.1 and 13.7 degrees 2-theta±0.2 degrees 2-theta; a PXRD pattern as depicted in FIG. 1; or combinations of these data.

Figure 6:
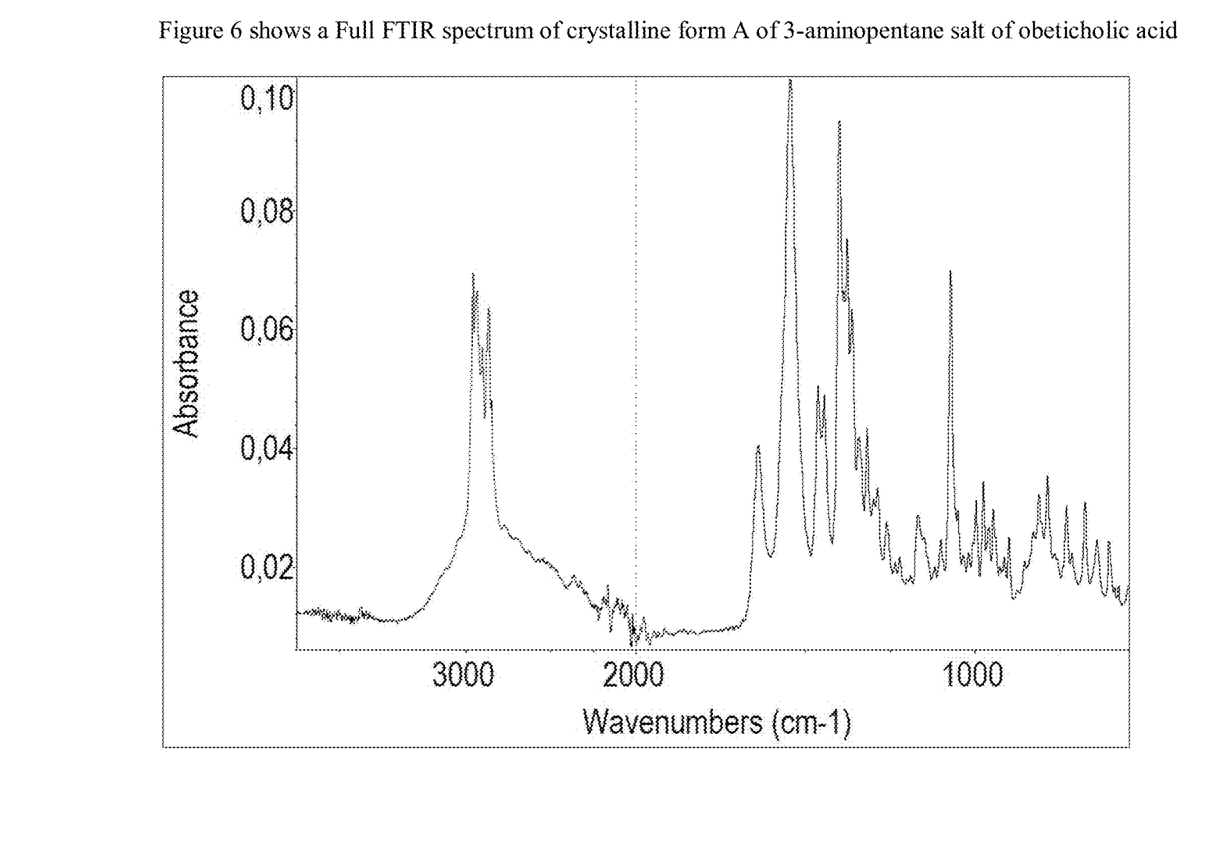
FIG. 6 shows a Full FTIR spectrum of 3-aminopentane salt of obeticholic acid
Figure 7:
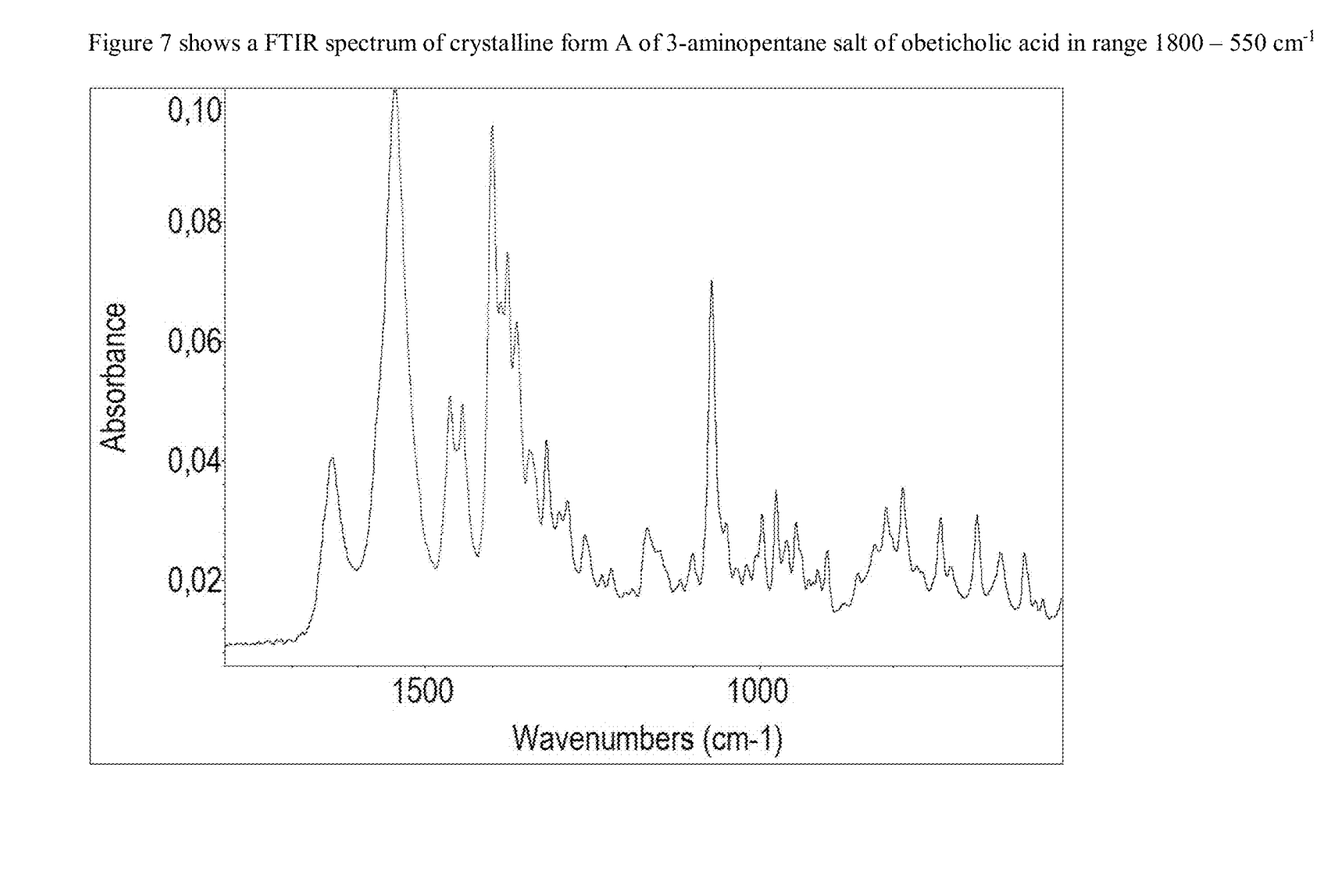
FIG. 7 shows a FTIR spectrum of 3-aminopentane salt of obeticholic acid in range 1800-550 $cm^1$.

Crystalline Form A of 3-aminopentane salt of obeticholic acid may be further characterized by the PXRD pattern having peaks at 5.3, 8.5, 10.8, 11.1 and 13.7 degrees 2-theta±0.2 degrees 2-theta, and also having one, two, three, four or five additional peaks at 12.9, 16.1, 16.7, 17.2 and 19.3 degrees 2-theta±0.2 degrees 2-theta; an FTIR spectrum having one, two, three, four or five peaks selected from 1639, 1545, 1400, 1319 and 1072±4 cm$^{-1}$; an FTIR spectrum as depicted in FIG. 6, an FTIR spectrum as depicted in FIG. 7 and combinations of these data.

Figure 1:
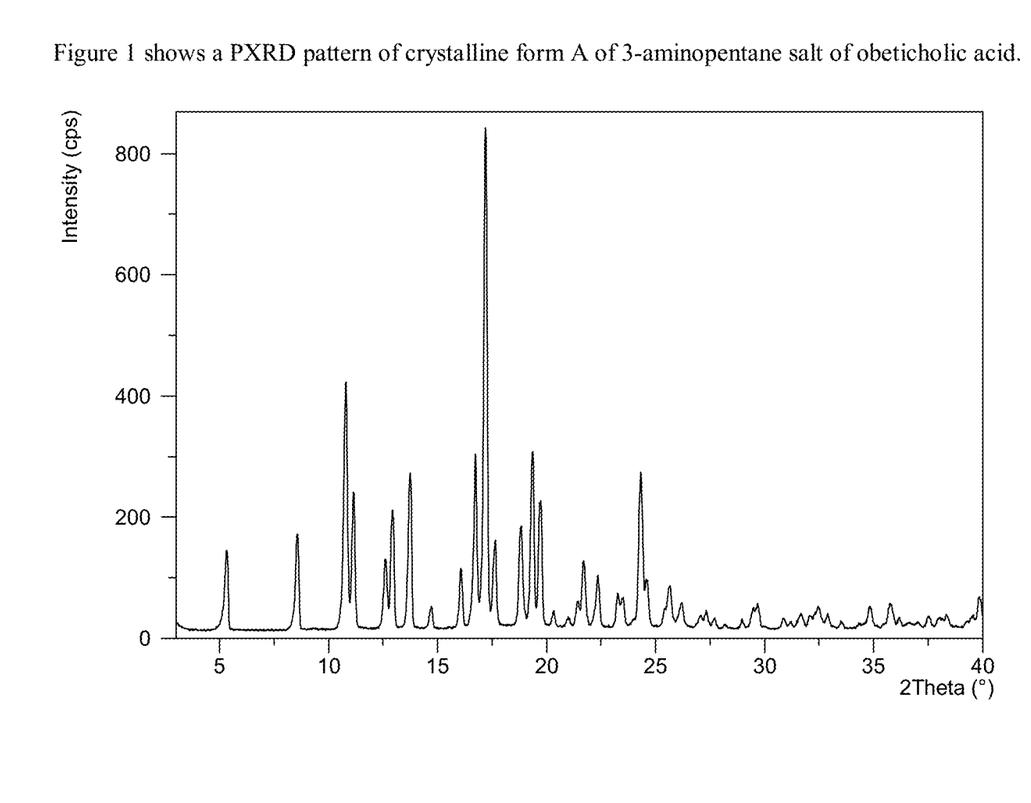
FIG. 1 shows a powder X-ray diffraction pattern ("powder XRD" or "PXRD") of 3-aminopentane salt of obeticholic acid obtained in Example 1.

Crystalline Form A of 3-aminopentane salt of obeticholic acid may be characterized by each of the above characteristics alone/or by all possible combinations, e.g., by PXRD pattern having peaks at 5.3, 8.5, 10.8, 11.1 and 13.7 degrees 2-theta±0.2 degrees 2-theta and a PXRD pattern as depicted in FIG. 1.

Crystalline Form A of 3-aminopentane salt of obeticholic acid according to any of the above embodiments may be an anhydrous form.

The present disclosure comprises (S)-3-aminoquinuclidine salt of obeticholic acid. Specifically, the present disclosure comprises crystalline (S)-3-aminoquinuclidine salt of obeticholic acid.

The present disclosure further comprises a crystalline form of (S)-3-aminoquinuclidine salt of obeticholic acid designated as Form A. The crystalline Form A of (S)-3-aminoquinuclidine salt of obeticholic acid can be characterized by data selected from one or more of the following: a PXRD pattern having peaks at 6.5, 8.9, 10.4, 13.9 and 14.5 degrees 2-theta±0.2 degrees 2-theta; a PXRD pattern as depicted in FIG. 2; or combinations of these data.

Crystalline Form A of (S)-3-aminoquinuclidine salt of obeticholic acid may be further characterized by the PXRD pattern having peaks at 6.5, 8.9, 10.4, 13.9 and 14.5 degrees 2-theta±0.2 degrees 2-theta, and also having one, two, three, four or five additional peaks at 16.1, 17.8, 18.3, 19.5 and 20.9 degrees 2-theta±0.2 degrees 2-theta.

Figure 2:
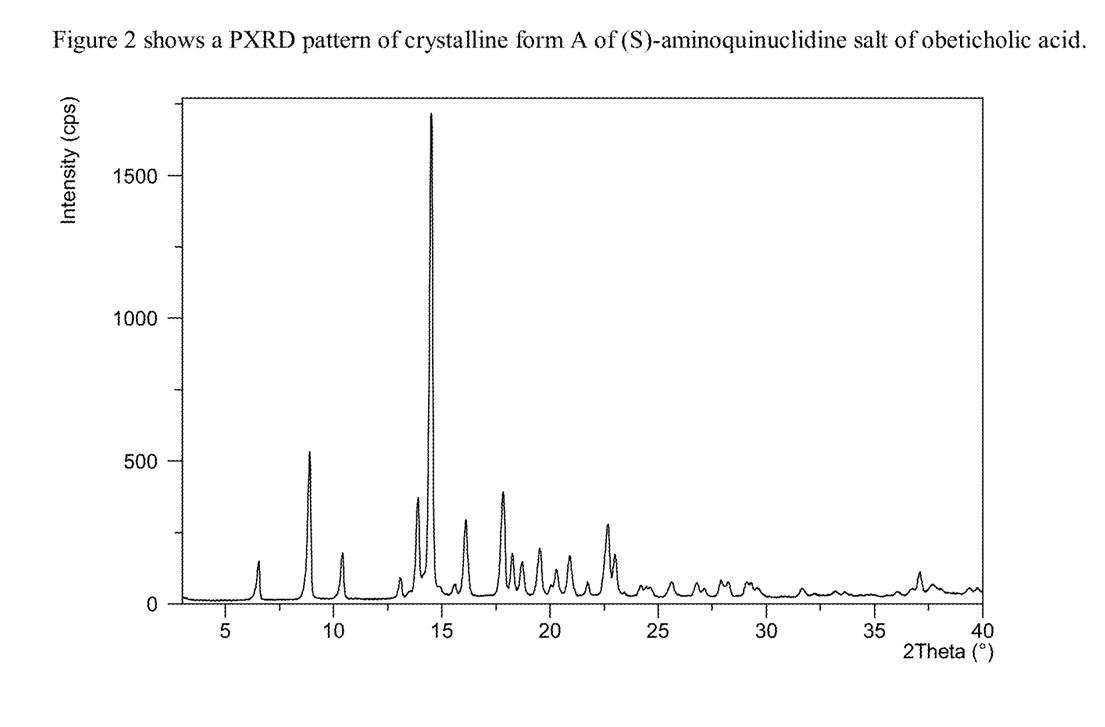
FIG. 2 shows a PXRD of crystalline form A (S)-3-aminoquinuclidine salt of obeticholic acid

Crystalline Form A of (S)-3-aminoquinuclidine salt of obeticholic acid may be characterized by each of the above characteristics alone/or by all possible combinations, e.g., by PXRD pattern having peaks at 6.5, 8.9, 10.4, 13.9 and 14.5 degrees 2-theta±0.2 degrees 2-theta and a PXRD pattern as depicted in FIG. 2.

The present disclosure comprises N-methyl propyl amine salt of obeticholic acid. Specifically, the present disclosure comprises crystalline N-methyl propyl amine salt of obeticholic acid.

The present disclosure further comprises a crystalline form of N-methyl propyl amine salt of obeticholic acid designated as Form A. The crystalline Form A of N-methyl propyl amine salt of obeticholic acid can be characterized by data selected from one or more of the following: a PXRD pattern having peaks at 9.0, 12.4, 19.1, 20.7 and 21.6 degrees 2-theta±0.2 degrees 2-theta; a PXRD pattern as depicted in FIG. 3; or combinations of these data.

Crystalline Form A of N-methyl propyl amine salt of obeticholic acid may be further characterized by the PXRD pattern having peaks at 9.0, 12.4, 19.1, 20.7 and 21.6 degrees 2-theta±0.2 degrees 2-theta, and also having one, two, three, four or five additional peaks at 4.9, 6.6, 14.2, 17.0 and 18.0 degrees 2-theta±0.2 degrees 2-theta.

Figure 3:
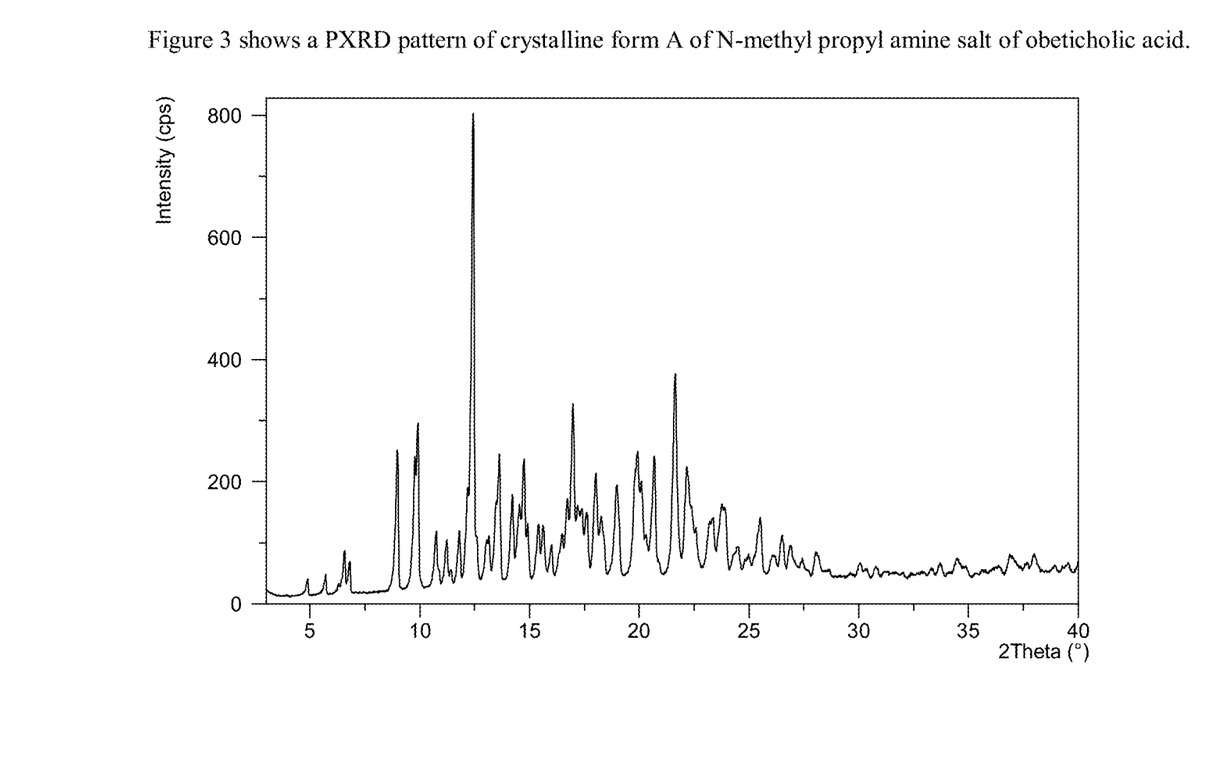
FIG. 3 shows a PXRD of crystalline form A N-methyl propyl amine salt of obeticholic acid

Crystalline Form A of N-methyl propyl amine salt of obeticholic acid may be characterized by each of the above characteristics alone/or by all possible combinations, e.g., by PXRD pattern having peaks at 9.0, 12.4, 19.1, 20.7 and 21.6 degrees 2-theta±0.2 degrees 2-theta and a PXRD pattern as depicted in FIG. 3.

The present disclosure comprises tetrabutylammonium salt of obeticholic acid. Specifically, the present disclosure comprises crystalline forms of tetrabutylammonium salt of obeticholic acid.

The present disclosure further comprises a crystalline form of tetrabutylammonium salt of obeticholic acid designated as Form A. The crystalline Form A of tetrabutylammonium salt of obeticholic acid can be characterized by data selected from one or more of the following: a PXRD pattern having peaks at 10.6, 11.9, 12.4, 12.8 and 13.3 degrees 2-theta±0.2 degrees 2-theta; a PXRD pattern as depicted in FIG. 4; or combinations of these data.

Crystalline Form A of tetrabutylammonium salt of obeticholic acid may be further characterized by the PXRD pattern having peaks at 10.6, 11.9, 12.4, 12.8 and 13.3 degrees 2-theta±0.2 degrees 2-theta, and also having one, two, three, four or five additional peaks at 8.4, 9.2, 15.5, 18.8 and 21.5 degrees 2-theta±0.2 degrees 2-theta.

Figure 4:
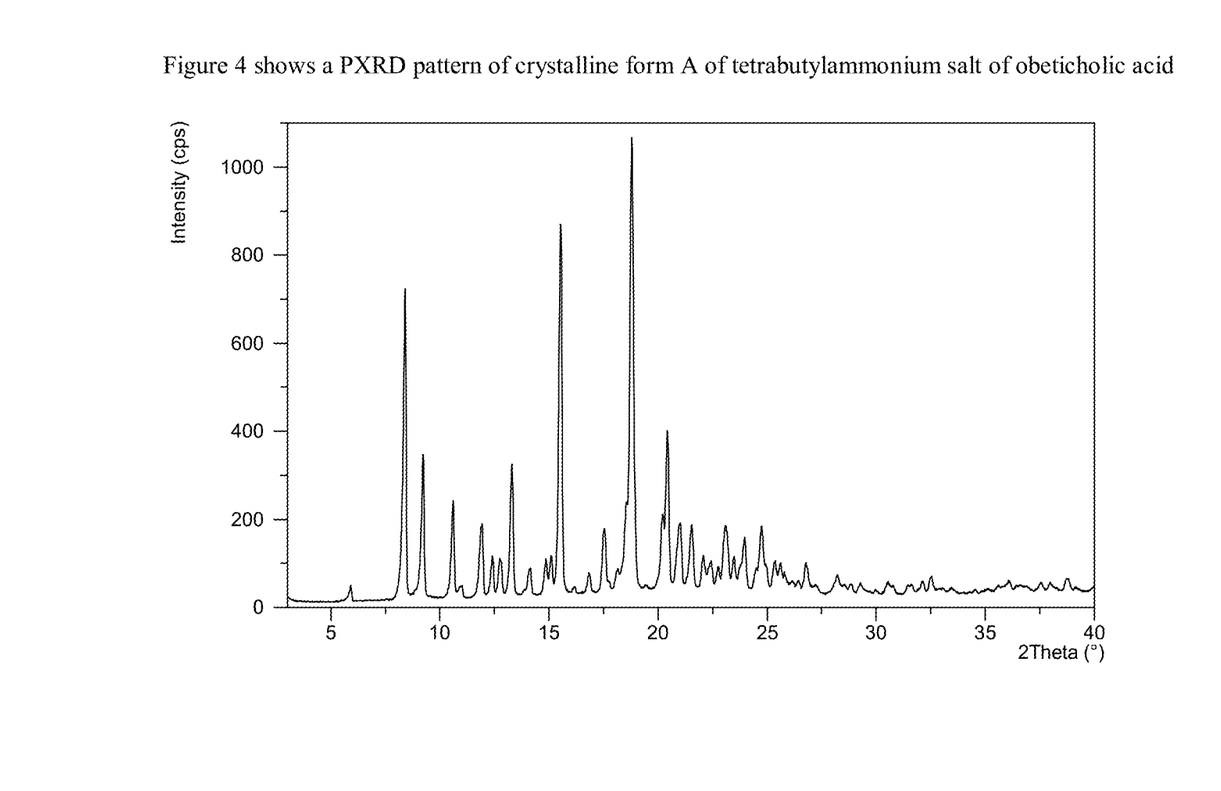
FIG. 4 shows a PXRD of crystalline form A of tetrabutylammonium salt of obeticholic acid

Crystalline Form A of tetrabutylammonium salt of obeticholic acid may be characterized by each of the above characteristics alone/or by all possible combinations, e.g., by PXRD pattern having peaks at 10.6, 11.9, 12.4, 12.8 and 13.3 degrees 2-theta±0.2 degrees 2-theta and a PXRD pattern as depicted in FIG. 4.

The present disclosure further comprises a crystalline form of tetrabutylammonium salt of obeticholic acid designated as Form B. The crystalline Form B of tetrabutylammonium salt of obeticholic acid can be characterized by data selected from one or more of the following: a PXRD pattern having peaks at 9.4, 10.8, 12.2, 13.1 and 13.5 degrees 2-theta±0.2 degrees 2-theta; a PXRD pattern as depicted in FIG. 5; or combinations of these data.

Crystalline Form B of tetrabutylammonium salt of obeticholic acid may be further characterized by the PXRD pattern having peaks at 9.4, 10.8, 12.2, 13.1 and 13.5 degrees 2-theta±0.2 degrees 2-theta, and also having one, two, three, four or five additional peaks at 8.4, 15.5, 18.6, 19.2 and 22.5 degrees 2-theta±0.2 degrees 2-theta.

Figure 5:
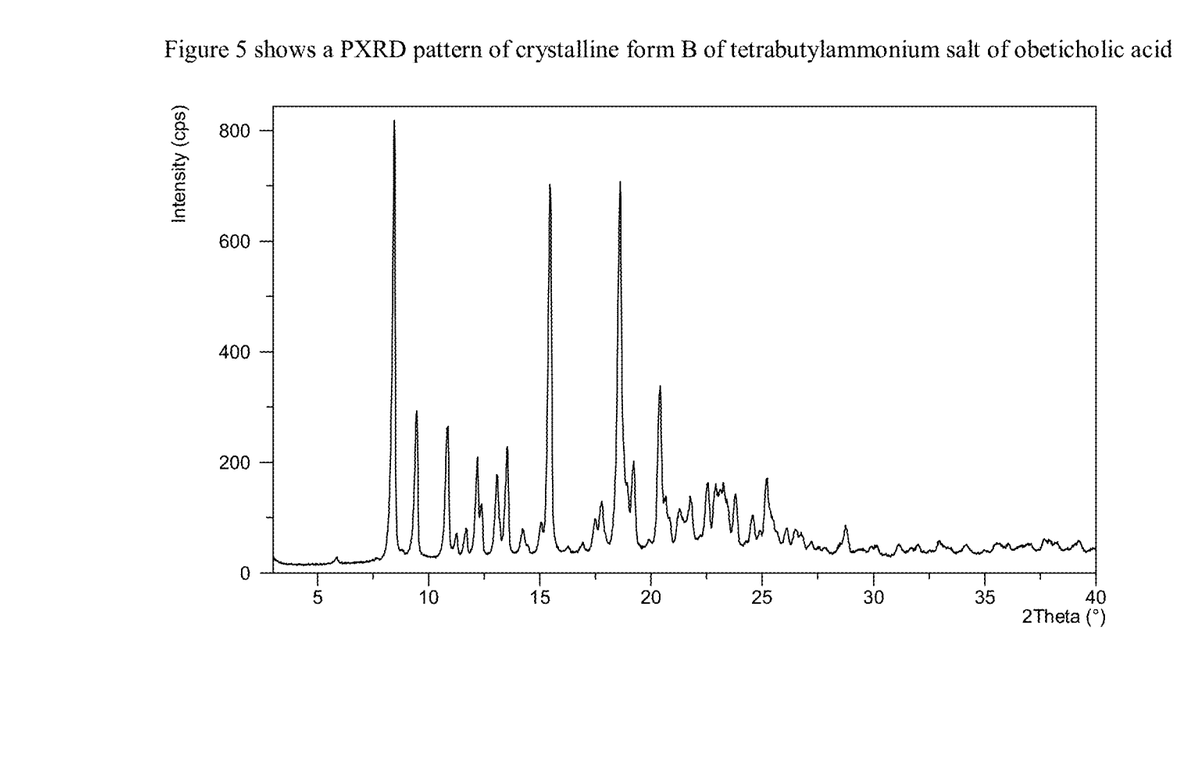
FIG. 5 shows a PXRD of crystalline form B of tetrabutylammonium salt of obeticholic acid

Crystalline Form B of tetrabutylammonium salt of obeticholic acid may be characterized by each of the above characteristics alone/or by all possible combinations, e.g., by PXRD pattern having peaks at 9.4, 10.8, 12.2, 13.1 and 13.5 degrees 2-theta±0.2 degrees 2-theta and a PXRD pattern as depicted in FIG. 5. The present disclosure also provides the use of obeticholic acid salts and the solid state forms thereof for preparing other solid state forms of Obeticholic acid, other salts of obeticholic acid and solid state forms thereof. In particular, the present disclosure provides use of crystalline forms of obeticholic acis salts according to the present invention e.g. crystalline forms of 3-aminopentane salt, (S)-3-aminoquinuclidine salt, N-methyl propyl amine salt and tetrabutylammonium salt of obeticholic acid for the preparation of amorphous form of obeticholic acid.

The present disclosure further encompasses processes for preparing Obeticholic acid or solid state forms thereof, e.g. an amorphous form. The process comprises preparing at least one of the solid state forms of the present disclosure, and converting it to Obeticholic acid. The conversion can be done, for example, by a process comprising reacting at least one of the obtained obeticholic acid salt e.g. 3-aminopentane salt of obeticholic acid with an appropriate acid to obtain obeticholic acid, in particular amorphous form of obeticholic acid.

In another embodiment the present disclosure encompasses the above described obeticholic acid salts (e.g. 3-aminopentane salt of obeticholic acid) and solid state forms thereof for use in the preparation of pharmaceutical compositions and/or formulations, preferably for the treatment of liver diseases, in particular primary biliary cirrhosis (PBC) and nonalcoholic steatohepatitis (NASH).

In another embodiment the present disclosure encompasses the use of the above described obeticholic acid salts (e.g. 3-aminopentane salt of obeticholic acid) and solid state forms thereof for the preparation of pharmaceutical compositions and/or formulations.

The present disclosure further provides pharmaceutical compositions comprising the obeticholic acid prepared according to the present disclosure, including amorphous form of obeticholic acid.

In yet another embodiment, the present disclosure encompasses pharmaceutical formulations comprising obeticholic acid prepared according to the present disclosure, including amorphous form of obeticholic acid and at least one pharmaceutically acceptable excipient.

Pharmaceutical formulations of the present invention contain any one or a combination of the solid state forms of obeticholic acid of the present invention, particularly amorphous obeticholic acid prepared according to the present invention. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and care-giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, the active ingredient and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of obeticholic acid is preferably formulated for administration to a mammal, preferably a human. Obeticholic acid can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The present disclosure encompasses a process to prepare said formulations of obeticholic acid comprising combining the obeticholic acid prepared according to the present disclosure, including amorphous form of obeticholic acid and at least one pharmaceutically acceptable excipient.

Obeticholic acid salts (e.g. 3-Aminopentane salt of obeticholic acid) and solid state forms thereof as defined herein, as well as the pharmaceutical compositions or formulations of obeticholic acid can be used as medicaments, particularly for the treatment of liver diseases, e.g. primary biliary cirrhosis (PBC) and nonalcoholic steatohepatitis (NASH).

The present disclosure also provides a method of treating of liver diseases, in particular primary biliary cirrhosis (PBC) and nonalcoholic steatohepatitis (NASH), comprising administering a therapeutically effective amount of obeticholic acid prepared according to the present disclosure, or at least one of the above pharmaceutical compositions or formulations, to a subject suffering from liver diseases, e.g. primary biliary cirrhosis (PBC) and nonalcoholic steatohepatitis (NASH), or otherwise in need of the treatment.

The present disclosure also provides the use of obeticholic acid salts (e.g. 3-aminopentane salt of obeticholic acid) and solid state forms thereof, amorphous form of obeticholic acid prepared according to the present disclosure, or at least one of the above pharmaceutical compositions or formulations for the manufacture of a medicament for treating liver diseases, in particular primary biliary cirrhosis (PBC) and nonalcoholic steatohepatitis (NASH).

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Analytical Methods

Powder X-Ray Diffraction Pattern ("PXRD") Method:

Prior to analysis, the samples were gently ground using a mortar and pestle to obtain a fine powder. Optionally, silicon powder can be added in a suitable amount as internal standard in order to calibrate the positions of the diffractions. The ground sample was adjusted into a cavity of the sample holder and the surface of the sample was smoothed using a glass slide. Powder X-ray Diffraction was performed on an X-Ray powder diffractometer PANalytical X'Pert Pro; CuKα radiation ($\lambda$=1.541874 Å); X'Celerator detector; laboratory temperature 25±3° C.; zero background sample holders.

Measurement Parameters:
Scan range 3-40 degrees 2-theta
Scan mode continuous
Step size 0.0167 degrees
Step size 42 s
Sample spin 60 rpm
Sample holder zero background silicon plate
Fourier Transform Infrared Spectroscopy ("FTIR") Method:
Equipment: Nicolet 380 FTIR Spectrometer
Mode: ATR (diamond);
Spectral range: 4000-550 cm-1;
Sample/bckg gain: 8.0;
Number of scans: 128;
Resolution: 4.0 cm-1.
Thermogravimetric analysis (TGA) method:
Thermogravimetric analysis was carried out on TA Instruments Discovery TGA with heating rate of 10° C./min in the range of 25°–250° C. and purged with 50 ml/min of nitrogen. An aluminium pan was used and the sample mass was about 5 mg.

EXAMPLES

Example 1: Preparation of Crystalline Form A of 3-Aminopentane Salt of Obeticholic Acid Into 150 mL-glass reactor equipped with a propeller stirrer and reflux condenser 2.0 g (4.755 mmol) of crude obeticholic acid was put and then 50 mL of n-butyl acetate was added. The content of the vessel was heated to 40° C., resulting in dissolution of obeticholic acid. The solution in the reactor was cooled down to 30° C. and 422.4 mg of 3-aminopentane (4.85 mmol) in 10 mL of butyl acetate was added dropwise into the reactor. The reactor content was warmed up to 90° C. over 30 minutes to obtain a solution. The clear solution was kept at 90° C. for about 30 minutes and then cooled down according to linear cooling ramp from 90° C. to 15° C. during 100 minutes. In the course of cooling ramp, a crystalline product was forming. After reaching the final temperature (15° C.) the slurry was still stirred for about 2 hours and then the solid phase was separated on small metal nutsch filter. The final drying was performed overnight by passing nitrogen through the filter at room temperature. It was obtained 2.32 g (95.9%) of white powder that is a 3-aminopentane salt of obeticholic acid, as confirmed by PXRD, DSC and TGA measurements.

Example 2: Preparation of Crystalline Form A of (S)-Aminoquinuclidine Salt of Obeticholic Acid Into 150 mL-glass reactor equipped with a propeller stirrer and reflux condenser 2.0 g (4.755 mmol) of obeticholic acid was placed and then 20 mL of isopropanol was added. The content of the vessel was heated to 40° C., resulting in dissolution of obeticholic acid. 975 mg (4.9 mmol) of (S)-3-aminoquinuclidine dihydrochloride was dissolved in 10 mL of water and passed through a small column with an anion exchange resin (10 mL, the total exchange capacity 3.2 eq/L) and after then rinsed with water to the total eluate volume of 40 mL (the last leaving eluate is neutral). The aqueous eluate with free base was added slowly to the obeticholic acid solution inside the reactor. The reactor content was heated slowly to reflux (81-82° C.) and refluxed for 60 minutes. In the reactor is a limpid solution that was then cooled down according to linear cooling ramp to 25° C. during 30 minutes. The solution was evaporated on Rotary Vacuum Evaporator (70° C. in the bath) until dry. An amorphous residue (2.62 g) was obtained. The amorphous solid was dissolved with 30 mL of ethyl acetate under heating. The solution was then allowed to cool freely; the salt is precipitated in the form of an amorphous mass and the slurry was placed in a refrigerator till the transformation an amorphous into crystalline was complete (roughly three months). The solid phase was separated on small metal filter. The final drying was performed overnight by passing nitrogen through the filtration cake at room temperature. It was obtained 2.21 g (85.0%) of white powder that is a salt of obeticholic acid and (S)-aminoquinuclidine.

Example 3: Preparation of Crystalline Form A of N-Methyl Propyl Amine Salt of Obeticholic Acid Into 150 mL-glass reactor equipped with a propeller stirrer and reflux condenser 2.0 g (4.755 mmol) of obeticholic acid was put and then 20 mL of butyl acetate was added. The content of the vessel was heated to 70° C., resulting in dissolution of obeticholic acid. The solution in the reactor was cooled down to 30° C. and 354.7 mg of methyl propyl amine (4.85 mmol) in 10 mL of butyl acetate was added dropwise into the reactor. Immediately during the addition of the amine, a white suspension of an amorphous salt is formed, which is passed in some time into a gel like mass and adhered to the walls of the reactor. The reactor content was warmed up to 70° C. over 30 minutes, during which time the amorphous phase was being dissolved. The clear solution was kept at 70° C. for about 30 minutes and then cooled down according to linear cooling ramp from 70° C. to 20° C. during 100 minutes. The amorphous slurry was being placed in a refrigerator until the conversion to the crystalline phase was completed (roughly three months), which could be observed visually. After then the solid phase was separated on small metal filter. The final drying was performed overnight by passing nitrogen through the filtration cake at room temperature. It was obtained 2.03 g (86.5%) of white powder that is a salt of obeticholic acid and N-methyl propyl amine.

Example 4: Preparation of Crystalline Form A of N-Methyl Propyl Amine Salt of Obeticholic Acid Into 150 mL-glass reactor equipped with a propeller stirrer and reflux condenser 2.0 g (4.755 mmol) of obeticholic acid was placed and then 20 mL of butyl acetate was added. The content of the vessel was heated to 70° C., resulting in dissolution of obeticholic acid. The solution in the reactor was cooled down to 20° C. and 354.7 mg of methyl propyl amine (4.85 mmol) in 10 mL of butyl acetate was added dropwise into the reactor. Immediately during the addition of the amine, a white suspension of an amorphous salt was formed. The reactor content was warmed up to 70° C. over 30 minutes, during which time the amorphous phase was being dissolved. The clear solution was kept at 70° C. for about 30 minutes and then cooled down according to linear cooling ramp from 70° C. to 20° C. in the course of 100 minutes. The salt is precipitated in the form of amorphous mass after cooling. Once the amorphous phase has appeared, the slurry was seeded with a small amount of the obeticholic acid N-methyl propyl amine crystalline salt (prepared e.g. according to example 3), and after achieving 20° C. stirred at this temperature for 2 hours, during which time the crystallization has being begun. It was allowed to complete overnight, leaving the slurry in the reactor without stirring at room temperature. In the morning, the crystalline suspension was stirred again 2 hours and then the solid phase was separated on small metal filter. The final drying was performed overnight inside the filter under nitrogen stream at room temperature. It was obtained 2.26 g (96.3%) of white product that is a salt of obeticholic acid and N-methyl propyl amine.

Example 5: Preparation of Crystalline Form A of N-Methyl Propyl Amine Salt of Obeticholic Acid Into 150 mL-glass reactor equipped with a propeller stirrer and reflux condenser 2.0 g (4.755 mmol) of crude obeticholic acid (HPLC content 93%) was placed and then 20 mL of butyl acetate was added. The content of the vessel was heated to 70° C., resulting in dissolution of obeticholic acid. The solution in the reactor was cooled down to 20° C. and 354.7 mg of methyl propyl amine (4.85 mmol) in 10 mL of butyl acetate was added dropwise into the reactor. Immediately during the addition of the amine, a white suspension of an amorphous salt was formed. The reactor content was warmed up to 70° C. over 30 minutes, during which time the amorphous phase was being dissolved. The clear solution was kept at 70° C. for about 30 minutes and then cooled down according to linear cooling ramp from 70° C. to 20° C. in the course of 100 minutes. The salt is precipitated in the form of an amorphous mass after cooling. Once the amorphous phase has appeared, the slurry was seeded with a small amount of the obeticholic acid N-methyl propyl amine crystalline salt (prepared e.g. according to example 3), and after achieving 20° C. stirred at this temperature for 2 hours. During this time the crystallization has being begun; compared to using the pure raw material the crystallization proceeds more slowly, the amorphous slurry for satisfactory crystallization must be left in the reactor at room temperature for 36 hours and even then amorphous deposits remain on the reactor surface, mainly on the stirrer. The next-next day (roughly 36 hours), the crystalline suspension was stirred again 2 hours and then the solid phase was separated on small metal filter. The final drying was performed overnight inside the filter under nitrogen stream at room temperature. It was obtained 1.67 g (69.9%) of white product that is a salt of obeticholic acid and N-methyl propyl amine. The HPLC content 97%.

Example 6: Preparation of Crystalline Form A of Tetrabutylammonium Salt of Obeticholic Acid Into 150 mL-glass reactor equipped with a propeller stirrer and reflux condenser 1.0 g (2.378 mmol) of obeticholic acid was placed and then 20 mL of isopropanol was added. The content of the vessel was heated to 40° C. resulting in dissolution of obeticholic acid. 823.37 mg (2.45 mmol) of tetrabutylammonium hydrogensulphate was dissolved in 10 mL of water and passed through a small column with an anion exchange resin (10 mL, the total exchange capacity 3.2 eq/L) and after then rinsed with water to the total eluate volume of 40 mL (the last leaving eluate is neutral). The aqueous eluate with free base was added slowly to the obeticholic acid solution inside the reactor. The reactor content was heated slowly to reflux (81-82° C.) and refluxed for 30 minutes. In the reactor is a limpid solution that was then cooled down according to linear cooling ramp to 25° C. during 100 minutes. The solution was evaporated on Rotary Vacuum Evaporator (70° C. in the bath) until dry. An amorphous glassy residue (1.20 g) was obtained, which was dissolved in a mixture of ethyl acetate and n-butyl acetate (30 mL+30 mL) under heating. The solution was then allowed to cool freely; the salt is precipitated in form of an amorphous mass after cooling. The amorphous slurry was placed in a refrigerator for the necessary time, roughly three months. After the crystalline conversion was finished the solid phase was separated on small metal filter. The final drying was performed overnight by passing nitrogen through the filtration cake at room temperature. It was obtained 1.47 g (93.2%) of white product that is a tetrabutylammonium salt of obeticholic acid.

Example 7: Preparation of Crystalline Form B of Tetrabutylammonium Salt of Obeticholic Acid Into 150 mL-glass reactor equipped with a propeller stirrer and reflux condenser 2.0 g (4.755 mmol) of obeticholic acid was placed and then 40 mL of isopropanol was added. The content of the vessel was heated to 40° C. resulting in dissolution of obeticholic acid. 1646.8 mg (4.85 mmol) of tetrabutylammonium hydrogensulphate was dissolved in 20 mL of water and passed through a small column with an anion exchange resin (10 mL, the total exchange capacity 3.2 eq/L) and after then rinsed with water to the total eluate volume of 80 mL (the last leaving eluate is neutral). The aqueous eluate with free base was added slowly to the obeticholic acid solution inside the reactor. The reactor content was heated slowly to 60° C. (the entire solid dissolved). The limpid solution was evaporated on Rotary Vacuum Evaporator (70° C. in the bath) until dry. The amorphous glassy residue (3.29 g) was obtained. The amorphous solid was dissolved in a mixture of Ethyl acetate and Isopropanol (60 mL+3 mL) under heating. The solution was then seeded with a small amount of form A of tetrabutylammonium salt of obeticholic acid (prepared e.g. according to example 6) and allowed to cool freely; the salt is precipitated in a crystalline form. The suspension was left to stay in refrigerator for two days and after then the solid phase was separated on small metal filter. The final drying was performed overnight by passing nitrogen through the filtration cake at room temperature. It was obtained 2.64 g (83.8%) of white powder that is a tetrabutylammonium salt of obeticholic acid.

Example 8: Preparation of Crystalline Form B of Tetrabutylammonium Salt of Obeticholic Acid Into 150 mL-glass reactor equipped with a propeller stirrer and reflux condenser 2.0 g (4.755 mmol) of crude obeticholic acid (HPLC content 86.6%) was placed and then 40 mL of isopropanol was added. The content of the vessel was heated to 40° C. resulting in dissolution of obeticholic acid. 1646.8 mg (4.85 mmol) of tetrabutylammonium hydrogensulphate was dissolved in 20 mL of water and passed through a small column with an anion exchange resin (10 mL, the total exchange capacity 3.2 eq/L) and after then rinsed with water to the total eluate volume of 80 mL (the last leaving eluate is neutral). The aqueous eluate with free base was added slowly to the obeticholic acid solution inside the reactor. The reactor content was heated slowly to 60° C. (the entire solid dissolved). The limpid solution was evaporated on Rotary Vacuum Evaporator (70° C. in the bath) until dry. The amorphous glassy residue (3.29 g) was obtained. The amorphous solid was dissolved in a mixture of ethyl acetate and isopropanol (60 mL+3 mL) under heating. The solution was then seeded with a small amount of form A of tetrabutylammonium salt of obeticholic acid (prepared e.g. according to example 6) and allowed to cool freely; the salt is precipitated in a crystalline form. The suspension was left to stay in refrigerator for two days and after then the solid phase was separated on small metal filter. The final drying was performed overnight by passing nitrogen through the filtration cake at room temperature. It was obtained 2.62 g (83.2%) of white powder that is a tetrabutylammonium salt of obeticholic acid. The HPLC purity of the obtained crystalline material was 93.5%.

Example 9: Preparation of Crystalline Form a of 3-Aminopentane Salt of Obeticholic Acid Into 1500 mL-double jacketed glass reactor equipped with a propeller stirrer and reflux condenser a solution of crude obeticholic acid 45.3 g (107.7 mmol; with recalculated content of pure obeticholic acid 86.16 mmol) in 320 mL ethyl acetate was placed*). After then an additional amount of ethyl acetate (1076 mL) was put in for dilution. The content of the vessel was heated to 30° C. To the solution in the reactor 9.58 g of 3-aminopentane (110.0 mmol) in 155 mL of ethyl acetate was added dropwise into the reactor. The reactor content was warmed up to 76° C. and kept at gentle reflux for 30 minutes—in the course of this warming and stirring the crystalline salt has begun to appear. The slurry was cooled down according to linear cooling ramp from 76° C. to 15° C. during 120 minutes. In the course of cooling ramp, the crystallization was finished. After reaching the final temperature (15° C.) the slurry was left to granulate for about 2 hours and then the solid phase was separated on c Nutsch filter. The final drying was performed overnight by passing nitrogen through the filter at room temperature. It was obtained 45 g (88.63 mmol) of white crystalline powder that is a 3-aminopentane salt of obeticholic acid.

*) this raw material originated from the previous synthetic step was used as solution without isolation.

The obtained material was used for repeated crystallization.

Example 10: Purification of Crystalline 3-Aminopentane Salt of Obeticholic Acid

Into 1500 mL-double jacketed glass reactor equipped with a propeller stirrer and reflux condenser 45.0 g (88.63 mmol) 3-aminopentane salt of obeticholic acid was loaded. Then 950 mL of toluene and 50 mL of isopropanol were added. The suspension inside the reactor was heated up to 92° C. in the course of 35 minutes. The solution was then cooled down according to linear cooling ramp from 92° C. to 20° C. during 12 hrs. It is useful to add a small amount of seed at 88° C. but this is not absolutely necessary. After reaching the final temperature (20° C.) the slurry was left to granulate for about 2 hours and then the solid phase was separated on stainless steel Nutsch filter. The final drying was performed overnight by passing nitrogen through the filter at room temperature. This above mentioned procedure was repeated three times—the output of the previous step is used as input to the next one—until the content of all critical impurities (monitored by HPLC) dropped below 0.1%.

The average yield of single crystallization step was 92.3%.

The overall yield of all (three) steps was 35.4 g (78.6%).

The obtained material is used for back conversion into obeticholic acid.

Monitoring of elimination some critical impurities during repeated crystallizations of obeticholic acid 3-aminopentane salt:

7-epi-obeticholic acid 0.96%=>0.07%
Dehydro-7-epi-obeticholic acid 0.07%=>0.00%
6,7-iso-obeticholic acid 0.76%=>0.05%

Example 11: Back Conversion of 3-Aminopentane Salt into Obeticholic Acid Amorphous Into 1500 mL-double jacketed glass reactor equipped with a propeller stirrer 33.2 g (65.38 mmol) 3-aminopentane salt of obeticholic acid was loaded. Then 330 mL of water and 462 mL of MTBE (methyl t-butyl ether) were added. Gradually, 72 mL of 5% $H_2SO_4$ w/w (which is roughly 72.4 mmol) was added under monitoring the pH. The pH after this addition was 2.2. It was stirred (extracted) for about 10 minutes then stirring was turned off and allowed the phases to settle. The phases were separated. 33 mL of water are added to the organic phase in the reactor and the organic layer is washed. The lower aqueous layer was combined with the raffinate. The main extract was put aside. The aqueous raffinate was extracted once more with 462 mL of MTBE during 10 minutes. After then, the phases were allowed to settle and were separated again. The organic phase was washed again with 33 mL of water (removal of potential traces of acid). The both organic extracts were combined. After then the organic layer was evaporated on RVO in a 2 L flask and foamed (the foam is very bulky). Parameters of the evaporation—bath 65° C., pressure at the beginning of 350 mBar. Obtained: 27.51 g (65.38 mmol) of obeticholic acid as dry amorphous foam. In this operation, the spectrum of accompanying impurities is virtually unchanged, only the salt is decomposed.

Example 12: Preparation of Crystalline Form a of 3-Aminopentane Salt of Obeticholic Acid (3-Pentylammonium Obeticholate)

Into a 10 L-double jacketed glass reactor equipped with an anchor stirrer and reflux condenser a solution of purified obeticholic acid (500 g dry-matter, 1.189 mol) in 16 L toluene-acetone mixture was stepwise placed*). The volume of warmed solution was stepwise reduced under vacuum to approx. 5 L. Then toluene (3 L) was added and the volume was again reduced to 6 L. After that toluene (7.4 L), 2-propanol (670 mL) and 3-aminopentane (109 g, 1.248 mol) was added and the reactor content was heated up to 90° C. to form a clear solution. Then the solution temperature was adjusted to 88-89° C. and afterward the seeding with crystalline 3-pentylammonium obeticholate (1 g) in toluene (50 mL) was done. After 15 minutes of stirring, the cooling linear ramp with final temperature 18° C. and the duration of 12 hours was started. After the end of the cooling ramp run, the obtained suspension was stirred for additional 3-4 hours at 18-20° C. The solid product was separated by filtration. The filter cake was rinsed twice with toluene (total 1 L) and then it was dried under stream of nitrogen at RT for approx. 12 hours. The yield of the process was 516 g (85.5% of theory) white crystalline powder of 3-pentylammonium obeticholate. The obtained material was used for repeated crystallization. ≠*) this material originated from the previous purification step by column chromatography was used as solution without isolation.

Example 13: Preparation of Crystalline Form a of 3-Aminopentane Salt of Obeticholic Acid (3-Pentylammonium Obeticholate)

Into a 10 L-double jacketed glass reactor equipped with an anchor stirrer and reflux condenser a solution of purified obeticholic acid (365 g dry-matter, 0.868 mol) in 14.5 L toluene-acetone mixture was stepwise placed*). The volume of warmed solution was stepwise reduced under vacuum to approx. 3.3 L. After that toluene (3.9 L) was added and the reactor content was heated up to 100° C. to form a clear solution. The addition of 3-aminopentane (93.3 g, 1.07 mol) in toluene (50 mL) was done. After about 2 minutes, the solution was seeded with the suspension of 3-pentylammonium obeticholate (0.45 g) in toluene (50 mL) at about 99° C. The forming suspension was stirred for next 30 minutes at about 98-99° C. and then was cooled down within approx. 1 hour to 18-20° C. The suspension was stirred additional 2 hours at 18-20° C. The solid product was separated by filtration. The filter cake was rinsed twice with toluene (total 800 mL) and then it was dried under stream of nitrogen at RT for approx. 12 hours. The yield of the process was 415 g (94.2% of theory) white crystalline powder of 3-pentylammonium obeticholate.

*) this material originated from the previous purification step by column chromatography was used as solution without isolation.

The obtained material was used for repeated crystallization.

Example 14: Purification (Repeated Crystallization) of Crystalline 3-Aminopentane Salt of Obeticholic Acid (3-Pentylammonium Obeticholate)

Into a 10 L-double jacketed glass reactor equipped with an anchor stirrer and reflux condenser 450 g (0.886 mol) 3-pentylammonium obeticholate was loaded. Then toluene (9.6 L) and 2-propanol (510 mL) was added. The suspension inside the reactor was heated up to 92-95° C. and stirred at this temperature until the clear solution was obtained. Then the solution temperature was adjusted to 88-89° C. and afterward the seeding 3-pentylammonium obeticholate (0.9 g) and a mixture of 3-aminopentane (2.3 g) in toluene (50 mL) was added. After 15 minutes of stirring, the cooling linear ramp with final temperature 18° C. and the duration of 12 hours was started. After the end of the cooling ramp run, the obtained suspension was stirred for additional 2-3 hours at 18-20° C. The solid product was separated by filtration. The filter cake was rinsed twice with toluene (total 0.9 L) and then it was dried under stream of nitrogen at RT for approx. 6 hours. The yield of the process was 405 g (89.9% of theory) white crystalline powder of 3-pentylammonium obeticholate.

The obtained material was used for repeated crystallization.

This above mentioned procedure was repeated six times—the output of the previous step is used as input to the next one—until the content of all critical impurities (monitored by HPLC) dropped below 0.1%.

The average yield of single crystallization step was 94.1%.

The overall yield of all (6) steps was 303 g (67.3%).

The purified 3-pentylammonium obeticholate is used for back conversion into obeticholic acid.

Monitoring of elimination some critical impurities during repeated crystallizations of 3-pentylammonium obeticholate:
7-epi-Obeticholic acid 1.77%→0.00%
Dehydro-obeticholic acid 1.15%→0.06%
6,7-iso-obeticholic acid 0.46%→0.02%
6-epi-Obeticholic acid 0.02%→0.08%

Example 15: Back Conversion of 3-Aminopentane Salt into Obeticholic Acid Amorphous Into a 10 L-double jacketed glass reactor equipped with an anchor stirrer and reflux condenser 352 g (0.693 mol)

3-aminopentane salt of obeticholic acid was loaded and water (2.5 L) was added. The suspension was stirred at RT and the solution of NaOH (33.3 g, 0.832 mol) in water (350 mL) was slowly added to reach clear solution with pH value about 12.5. The solution in the reactor was three times extracted with TBME (total 1.29 L). The volume of final aqueous phase (3.2 L) was warmed and vacuum reduced to 2.6 L, then water (0.6 L) was added.

Into next 10 L-double jacketed glass reactor equipped with an anchor stirrer and reflux condenser the solution of $H_3PO_4$ 85% (69 mL, 1.007 mol) in water (3.2 L) was charged and stirred at RT. The alkaline solution from the first reactor was slowly added into aqueous acid accompanied by the formation of a suspension with final pH value about 2.7. The solid product was separated by filtration. The filter cake was rinsed several times with water (total 5.5 L) until the filtrate reached a conductivity value less than 20 S and then it was dried under stream of nitrogen at RT for approx. 48 hours. Dried lumpy powder was comminuted on a sieve with a mesh size of 2 mm and the final drying was carried out in a vacuum dryer at about 50° C. for about 12 hours. The yield of the process was 289 g (99.1% of theory) white powder of amorphous obeticholic acid.

The invention claimed is:

1. Crystalline 3-aminopentane salt of obeticholic acid.
2. Crystalline 3-aminopentane salt of obeticholic acid according to claim 1, characterized by data selected from one or more of the following:
   (i) a PXRD pattern having peaks at 5.3, 8.5, 10.8, 11.1 and 13.7 degrees 2-theta±0.2 degrees 2-theta;
   (ii) a PXRD pattern having peaks at 5.3, 8.5, 10.8, 11.1 and 13.7 degrees 2-theta±0.2 degrees 2-theta, and also having one, two, three, four or five additional peaks at 12.9, 16.1, 16.7, 17.2 and 19.3 degrees 2-theta±0.2 degrees 2-theta;
   (iii) a PXRD pattern as depicted in FIG. 1;
   and combinations of any of (i)-(iii).
3. Crystalline 3-aminopentane salt of obeticholic acid according to claim 2, characterized by data selected from one or more of the following:
   (i) an FTIR spectrum having one, two, three, four or five peaks selected from 1639, 1545, 1400, 1319 and 1072±4 $cm^{-1}$;
   (ii) an FTIR spectrum as depicted in FIG. 6,
   (iii) an FTIR spectrum as depicted in FIG. 7
   and combinations of any of (i)-(iii).
4. Crystalline 3-aminopentane salt of obeticholic acid according to claim 1, which is an anhydrous form.
5. Crystalline 3-aminopentane salt of obeticholic acid according to claim 1, which is polymorphically pure.
6. A pharmaceutical composition or formulation comprising crystalline 3-aminopentane salt of obeticholic acid according to claim 1.
7. A pharmaceutical composition or formulation comprising crystalline 3-aminopentane salt of obeticholic acid according to claim 1 and at least one pharmaceutically acceptable excipient.
8. A process for preparing a pharmaceutical composition or formulation comprising combining the crystalline 3-aminopentane salt of obeticholic acid according to claim 1 and at least one pharmaceutically acceptable excipient.
9. A process for preparing a different solid state form of obeticholic acid or salt thereof comprising preparing crystalline 3-aminopentane salt of obeticholic acid according to claim 1 and converting it to a different solid state form of obeticholic acid or salt thereof.
10. A process for preparing amorphous form of obeticholic acid comprising preparing crystalline 3-aminopentane salt of obeticholic acid according to claim 1 and converting it amorphous form of obeticholic acid.
11. A method of treating a liver disease, comprising administering a therapeutically effective amount of the crystalline 3-aminopentane salt of obeticholic acid according to claim 1 to a subject suffering from a liver disease or otherwise in need of the treatment.
12. A method of treating a liver diseases, comprising administering a pharmaceutical composition or formulation according to claim 6 to a subject suffering from a liver disease or otherwise in need of the treatment.
13. The method of claim 11, wherein the liver disease is primary biliary cirrhosis (PBC) or nonalcoholic steatohepatitis (NASH).
14. The method of claim 12, wherein the liver disease is primary biliary cirrhosis (PBC) or nonalcoholic steatohepatitis (NASH).

* * * * *